(12) United States Patent
Kang et al.

(10) Patent No.: US 7,341,974 B2
(45) Date of Patent: *Mar. 11, 2008

(54) METHOD FOR PREPARING A CATALYST FOR PARTIAL OXIDATION OF PROPYLENE

(75) Inventors: Jung Hwa Kang, Seoul (KR); Won Ho Lee, Daejun (KR); Min Ho Kil, Pusan (KR); Hyun Jong Shin, Chulranam-Do (KR); Byung Yul Choi, Seoul (KR); Yeon Shick Yoo, Chulranam-Do (KR); Young Hyun Choe, Chulranam-Do (KR); Ju Yeon Park, Chulranam-Do (KR)

(73) Assignee: LG Chem, Ltd., Seoul (KR)

( * ) Notice: Subject to any disclaimer, the term of this patent is extended or adjusted under 35 U.S.C. 154(b) by 81 days.

This patent is subject to a terminal disclaimer.

(21) Appl. No.: 10/486,403

(22) PCT Filed: Jan. 3, 2003

(86) PCT No.: PCT/KR03/00005

§ 371 (c)(1),
(2), (4) Date: Feb. 11, 2004

(87) PCT Pub. No.: WO03/097233

PCT Pub. Date: Nov. 27, 2003

(65) Prior Publication Data

US 2004/0192545 A1    Sep. 30, 2004

(30) Foreign Application Priority Data

May 16, 2002 (KR) ................................ 2002-27023

(51) Int. Cl.
*B01J 23/00* (2006.01)
(52) U.S. Cl. ...................... 502/311; 502/313; 502/314; 502/315; 502/316; 502/321
(58) Field of Classification Search ................ 502/311, 502/313–317, 321, 255
See application file for complete search history.

(56) References Cited

U.S. PATENT DOCUMENTS

| | | | |
|---|---|---|---|
| 2,941,007 A | 6/1960 | Callahan et al. | |
| 3,089,909 A | 5/1963 | Barclay et al. | |
| 3,171,859 A | 3/1965 | Sennewald et al. | |
| 3,350,323 A * | 10/1967 | Willatt et al. | 502/244 |
| 3,522,299 A | 7/1970 | Takenaka et al. | |
| 3,825,600 A | 7/1974 | Ohara et al. | |
| 3,836,586 A * | 9/1974 | Yamada et al. | 568/477 |
| 4,224,187 A | 9/1980 | Vanderspurt | |
| 4,248,803 A | 2/1981 | Vanderspurt | |
| 4,442,308 A | 4/1984 | Arntz et al. | |
| 4,556,731 A * | 12/1985 | Guttmann et al. | 562/546 |
| 4,873,217 A | 10/1989 | Kawajiri et al. | |
| 5,017,542 A | 5/1991 | Martan et al. | |
| 5,059,573 A * | 10/1991 | Sasaki et al. | 502/205 |
| 5,245,083 A * | 9/1993 | Matsuura | 568/479 |
| 5,364,522 A * | 11/1994 | Wang | 205/50 |
| 5,532,199 A * | 7/1996 | Watanabe et al. | 502/311 |
| 5,602,280 A * | 2/1997 | Nagai et al. | 562/546 |
| 5,663,113 A * | 9/1997 | Midorikawa et al. | 502/314 |
| 5,728,894 A * | 3/1998 | Nagano et al. | 568/479 |
| 5,856,259 A * | 1/1999 | Watanabe et al. | 502/305 |
| 6,028,220 A * | 2/2000 | Wada et al. | 562/546 |
| 6,080,893 A | 6/2000 | Hecquet et al. | |
| 6,245,931 B1 * | 6/2001 | Aoki et al. | 558/324 |
| 6,281,384 B1 | 8/2001 | Contracter et al. | |
| 6,337,424 B1 | 1/2002 | Karim et al. | |
| 6,784,134 B2 * | 8/2004 | Kasuga et al. | 502/182 |
| 6,878,847 B2 * | 4/2005 | Kasuga et al. | 562/532 |
| 6,881,702 B2 * | 4/2005 | Arnold et al. | 502/311 |
| 2001/0021688 A1 | 9/2001 | Pollesel et al. | |

FOREIGN PATENT DOCUMENTS

| | | |
|---|---|---|
| CN | 1249327 A | 4/2000 |
| CN | 1317546 A | 10/2001 |
| JP | 43-27401 | 11/1968 |
| JP | 8-40969 A | 2/1996 |
| WO | WO 02/30569 A1 | 4/2002 |

* cited by examiner

*Primary Examiner*—Cam N. Nguyen
(74) *Attorney, Agent, or Firm*—Birch, Stewart, Kolasch & Birch, LLP

(57) ABSTRACT

The present invention relates to a method for preparing a catalyst for partial oxidation of propylene, particularly a method for preparing a catalyst for preparing an acrylic acid, using an organic acid such as a citric acid, maleic acid and oxalic acid. The complex oxide catalyst according to the invention, when used in the gas phase catalytic oxidation of propylene, may produce acrolein in high yield.

8 Claims, No Drawings

METHOD FOR PREPARING A CATALYST FOR PARTIAL OXIDATION OF PROPYLENE

FIELD OF THE INVENTION

The present invention relates to a catalyst used in the process for preparing acrolein and acrylic acid by reacting propylene with a gas-containing air or oxygen.

BACKGROUND OF THE INVENTION

An acrylic acid is produced by partially oxidizing propylene and then oxidizing tile resulting acrolein. This process is performed at the lowest possible oxygen concentration in order to maintain high selectivity of acrolein or acrylic acid, as well as to avoid the combustion resulted from the increased oxygen concentration in tile reactant and to prevent excess reaction. Complete oxidation such as production of CO and $CO_2$ at an elevated temperature causes reduction of the selectivity toward acrolein. Further, elevated reacting temperatures cause inactivation and volatilization of the active components and reduce the lifetime of the catalyst as well. Thus, if catalysts for preparing an acrylic acid have higher activity at a lower reaction temperature and higher selectivity toward the acrylic acid, they have higher commercial values.

A number of patent applications, which relate to catalysts used to produce acrolein by gas phase oxidation of propylene, have been filed to meet the commercial demands. For instance, U.S. Pat. No. 2,941,007 (J. L. Callahan et al.) discloses a catalyst comprising bismuth molybdate or bismuth phosphomolybdate. U.S. Pat. No. 3,171,859 (K. Sennewald et al.) discloses a catalyst consisting of Fe, Bi, P, Mo and O. U.S. Pat. No. 3,522,299 (S. Takenaka et al.) discloses a catalyst consisting of Ni, Co, Fe, Bi, Mo, P, As and O. U.S. Pat. No. 3,089,909 (J. L. Barclay et al.) discloses a catalyst selected from the group consisting of tin tungstate, tungstic acid and bismuth tungstate. In addition, U.S. Pat. No. 3,825,600 (T. Ohara et al.) discloses a catalyst containing Mo, Co, Fe, Bi, W, Si, alkali metal etc.

Even though some of these catalysts do not have yields sufficient to produce acrolein and acrylic acid to be applicable to the industry, improved catalysts have been proposed. For example, U.S. Pat. Nos. 4,873,217, 4,224,187, 4,248,803, 5,017,542 etc. proposed catalysts which have a higher conversion rate of propylene and improved yields of acrolein and acrylic acid by controlling the ingredients of a catalyst and their mixing ratio, and processes for producing the catalysts.

On the other hand, there have been developments in the methods for producing a acrolein and acrylic acid utilizing conventional catalysts of molybdenum-bismuth-cobalt-iron oxide compounds. However, further studies are increasingly needed to develop a process for producing a catalyst of molybdenum-bismuth-cobalt-iron oxide compounds which has higher activity and selectivity.

SUMMARY OF THE INVENTION

The object of the invention is to provide a process for producing a catalyst which has high selectivity toward acrolein and great activity for converting propylene, and which can be stably operated.

The inventors have discovered the fact that this object can be achieved by using a catalyst having the following formula I in the process for producing an acrylic acid by gaseous phase oxidation from a gas-containing acrolein.

$$Mo_aBi_bFe_cX_dY_eO_f \qquad (I)$$

wherein, X is at least one element selected from the group consisting of Co and Ni;
Y is at least one element selected from the group consisting of K and Rb; and
a, b, c, d, e and f represent an atomic ratio of each element, provided that when a is 12, b is 0.5 to 2, c is 0.5 to 2, d is 3 to 8, e is 0.005 to 0.2 and f is the value corresponding to the oxidation state of each element.

DETAILED DESCRIPTION OF THE INVENTION

When a catalyst is produced by a conventional co-precipitation process, layer separation occurs between metal salts. This layer separation makes it difficult to produce a catalyst with homogeneous composition. However, the present invention can easily solve the layer separation problem by using an organic acid such as a citric acid, maleic acid and oxalic acid and provide improved performance of a catalyst.

A suspension is prepared by dissolving the metal salts of a catalyst represented by the formula I one after another in an organic acid solution. The suspension is dried, ground, and calcined in the presence of air to obtain a catalyst. The amount of the organic acid added in the preparation of the catalyst must be properly controlled according to the total mole number of the nitrate anions of the metal salts. The amount of the organic acid should be preferably 0.5 to 10, more preferably 0.8 to 5.0 mole ratio based on the nitrate anion of the metal salts.

The organic acid should contain 1 to 10 carbon atoms and at least one of a hydroxyl group and a carboxyl group. Examples of the organic acid used in this invention are, but not limited to, citric acid, maleic acid and oxalic acid.

When used in commercial purpose, catalysts are molded into a certain size and shaped by conventional methods Such as extrusion.

There are no particular limits to the reaction conditions used in the present invention. The present invention can adopt conventional reaction conditions, which are useful in the preparation of acrolein and acrylic acid by gaseous phase catalytical oxidation of propylene in a fixed bed multi-tubular reactor.

The present invention will be described in detail by way of the following Examples and Experiments. The examples illustrate the invention without limiting its scope.

EXAMPLES

Preparation of Catalyst

Example 1

400 ml of distilled water was introduced into 500 cc of a glass reaction vessel, and stirred while heated to 75° C. 300 g of a citric acid was dissolved in the resulting solution. Sequentially, 100 g of ammonium molybdate, 19.7 g of ferric nitrate, and 54.95 g of cobalt nitrate were added and completely dissolved. A solution of 34.35 g of bismuth nitrate and 0.286 g of potassium nitrate in nitric acid was added to the resulting solution, and dried in a rotatory vacuum dryer. The dried catalyst cake was recovered and ground into a 40 mesh size to produce catalyst powder. The combined catalyst powder was calcined at 450° C. for 5 hours in the sintering furnace to produce a catalyst. The calcination was carried out in the presence of the air.

The composition of the catalyst was $Mo_{12}Bi_{1.5}Co_{4.4}Fe_2K_{0.06}$.

Comparative Example 1

300 ml of distilled water was introduced into a glass reaction vessel and heated to 75° C. 100 g of ammonium molybdate was dissolved. The solution of 19.7 g of ferric nitrate, 60.44 g of cobalt nitrate, 34.35 g of bismuth nitrate and 0.286 g of potassium nitrate in nitric acid was deposited into a solution of molybdate to produce a catalyst. The catalyst was dried in a vacuum drier. The combined dried cake was ground into a 40 mesh size to produce catalyst powder. The catalyst powder was calcined at 450° C. for 5 hours in the sintering furnace.

The composition of the catalyst was $Mo_{12}Bi_{1.5}Co_{4.4}Fe_2K_{0.06}$.

Example 2

400 ml of distilled water was introduced into 500 cc of a glass reaction vessel, and stirred while heated to 75° C. 400 g of maleic acid was dissolved in the resulting solution. Sequentially, 100 g of ammonium molybdate, 39.4 g of ferric nitrate, 60.44 g of cobalt nitrate were added and completely dissolved. A solution of 34.35 g of bismuth nitrate and 0.286 g of potassium nitrate in nitric acid was added to the resulting solution, and dried in a rotatory vacuum dryer. The drying and calcining processes are the same as Example 1.

The composition of the catalyst was $Mo_{12}Bi_{1.5}Co_{4.4}Fe_2K_{0.06}$.

Example 3

A catalyst was produced by the same processes as Example 1, except for the use of 300 g of an oxalic acid.

The composition of the catalyst was $Mo_{12}Bi_{1.5}Co_{4.4}Fe_2K_{0.06}$.

Experiment

Catalytic Activity Test

In the methods known to date, the conversion rate of propylene is over 90%, the selectivity toward acrolein and acrylic acid is 85 to 98%, and the yield of acrolein and acrylic acid is 77 to 98%. Since the conditions for a catalyst activity test vary, it is meaningless to compare the test results disclosed in prior art publications with each another.

To measure the activity of the catalyst produced by the present invention, the catalyst was made into a shape of pellet, placed into a reactor and subjected to the oxidation of propylene to yield acrolein and acrylic acid. For the production of acrolein and acrylic acid, the gas feed comprising 1 to 10% by volume of propylene, 1 to 15% by volume of oxygen, 5 to 60% by volume of water vapor and 20 to 80% by volume of inert gas was introduced over the catalyst bed at a temperature of 200 to 350° C., under a pressure of 1 to 3 bar and a space velocity (STP) of 500 to 5,000 hr. The results of the tests in the Examples and Comparative Example are shown in Table 1.

In the Examples, the conversion rate of propylene and the yield of acrolein are calculated by Equations 1 to 3.

Conversion rate of propylene (%)=[(mole number of reacted propylene)/(mole number of supplied propylene)]×100   Equation 1

Selectivity toward acrolein (%)=[(mole number of produced acrolein)/(mole number of reacted acrolein)]×100   Equation 2

Yield (%)=[(mole number of produced acrolein and acrylic acid)/(mole number of supplied propylene)]×100   Equation 3

TABLE 1

| Ex | Organic acid | Composition of catalyst | React Temp (° C.) | Conv. of propylene (%) | Selectivity toward acrolein (%) | Acrolein + acrylic acid yield(%) |
|---|---|---|---|---|---|---|
| 1 | citric acid | $Mo_{12}Bi_{1.5}Co_{4.4}Fe_2K_{0.06}$ | 320 | 98.12 | 82.53 | 91.05 |
| 2 | maleic acid | $Mo_{12}Bi_{1.5}Co_{4.4}Fe_2K_{0.06}$ | 320 | 97.52 | 81.64 | 90.12 |
| 3 | oxalic acid | $Mo_{12}Bi_{1.5}Co_{4.4}Fe_2K_{0.06}$ | 320 | 97.80 | 81.73 | 90.43 |
| C1 | — | $Mo_{12}Bi_{1.5}Co_{4.4}Fe_2K_{0.06}$ | 320 | 94.21 | 74.34 | 85.23 |

As shown in table 1, the present invention can produce a catalyst with high selectivity toward acrolein and acrylic acid, and good reproducibility by utilizing various organic acids.

We claim:

1. Method for preparing an unsupported catalyst of formula (I) for partial oxidation of propylene, comprising the step of adding salts of metal components constituting the catalyst to an aqueous solution containing organic acid having 1 to 10 carbon atoms for preventing layer separation to obtain a catalyst suspension:

$$Mo_aBi_bFe_cX_dY_eO_f \qquad (I)$$

wherein,

X is at least one element selected from the group consisting of Co and Ni;

Y is at least one element selected from the group consisting of K and Rb; and a, b, c, d, e and f represent the atomic ratio of each element, provided that when a is 12, then b is 0.5 to 2, c is 0.5 to 2, d is 3 to 8, e is 0.005 to 0.2 and f is the value corresponding to the oxidation state of each element.

2. Method according to claim 1, comprising:
(a) adding, to the aqueous salt solution containing organic acid having 1 to 10 carbon atoms, metal components comprising:
   (i) molybdenum,
   (ii) bismuth,
   (iii) iron,
   (iv) cobalt and/or nickel, and
   (v) potassium and/or rubidium to produce said catalyst suspension;
(b) drying the catalyst suspension in vacuo;
(c) grinding the dried catalyst suspension to produce a catalyst powder; and
(d) calcining the catalyst powder in the presence of air.

3. Method according to claim 1 wherein said organic acid having 1 to 10 carbon atoms is selected from the group consisting of citric acid, maleic acid and oxalic acid.

4. Method according to claim 1, wherein said adding step consists of adding salts of metal components constituting the catalyst to said aqueous solution containing organic acid having 1 to 10 carbon atoms to obtain said catalyst suspension.

5. Method according to claim 4, wherein said aqueous solution consists of water and organic acid containing 1 to 10 carbon atoms.

6. The method of claim 1, wherein said method consists essentially of:
(a) adding said salts of metal components constituting the catalyst to said aqueous solution containing organic acid having 1 to 10 carbon atoms for preventing layer separation to obtain a catalyst suspension;
(b) drying the catalyst suspension in vacuo;
(c) grinding the dried catalyst suspension to produce a catalyst powder; and
(d) calcining the catalyst powder in the presence of air.

7. The method according to claim 1, said method consisting essentially of:
(a) adding, to the aqueous sail solution containing organic acid having 1 to 10 carbon atoms, metal components comprising:
   (i) molybdenum,
   (ii) bismuth,
   (iii) iron,
   (iv) cobalt and/or nickel, and
   (v) potassium and/or rubidium to produce said catalyst suspension;
(b) drying the catalyst suspension in vacuo;
(c) grinding the dried catalyst suspension to produce a catalyst powder; and
(d) calcining the catalyst powder in the presence of air.

8. Method for preparing an unsupported catalyst of formula (I) for partial oxidation of propylene, comprising the step of
(a) preparing a catalyst suspension by an adding step consisting of adding an organic acid having 1 to 10 carbon atoms for preventing layer separation to an aqueous salt solution of metal components constituting the catalyst:

$$Mo_a Bi_b Fe_c X_d Y_e O_f \tag{I}$$

wherein,
X is at least one element selected from the group consisting of Co and Ni;
Y is at least one element selected from the group consisting of K and Rb;
a, b, c, d, e and f represent the atomic ratio of each element, provided that when a is 12, then b is 0.5 to 2, c is 0.5 to 2, d is 3 to 8, e is 0.005 to 0.2 and f is the value corresponding to the oxidation state of each element;
(b) drying the catalyst suspension in vacuo;
(c) grinding the dried catalyst suspension to produce a catalyst powder; and
(d) calcining the catalyst powder in the presence of air.

* * * * *